(12) United States Patent
Tang et al.

(10) Patent No.: US 8,052,612 B2
(45) Date of Patent: Nov. 8, 2011

(54) RESPIRATION MONITORING SYSTEM

(75) Inventors: Chien-Fa Tang, Taipei Hsien (TW); Ching-Tang Huang, Taipei Hsien (TW)

(73) Assignee: Taiwan Textile Research Institute, New Taipei (TW)

( * ) Notice: Subject to any disclaimer, the term of this patent is extended or adjusted under 35 U.S.C. 154(b) by 147 days.

(21) Appl. No.: 12/046,469

(22) Filed: Mar. 12, 2008

(65) Prior Publication Data
US 2008/0228097 A1 Sep. 18, 2008

(30) Foreign Application Priority Data
Mar. 12, 2007 (TW) .............................. 96108406 A

(51) Int. Cl.
*A61B 5/08* (2006.01)
(52) U.S. Cl. ......... 600/534; 600/529; 600/536; 600/388
(58) Field of Classification Search ................. 600/490, 600/499, 485, 488, 534, 491, 529, 388
See application file for complete search history.

(56) References Cited

U.S. PATENT DOCUMENTS

| | | | |
|---|---|---|---|
| 3,926,179 A * | 12/1975 | Petzke et al. | ................... 600/485 |
| 4,815,473 A | 3/1989 | Watson et al. | |
| 4,834,109 A | 5/1989 | Watson | |
| 6,011,477 A | 1/2000 | Teodorescu et al. | |
| 6,030,342 A * | 2/2000 | Amano et al. | ................. 600/301 |
| 6,341,504 B1 * | 1/2002 | Istook | .......................... 66/172 E |
| 6,450,957 B1 | 9/2002 | Yoshimi et al. | |
| 6,778,090 B2 | 8/2004 | Newham | |
| 6,829,942 B2 | 12/2004 | Yanai et al. | |
| 6,941,775 B2 * | 9/2005 | Sharma | .......................... 66/202 |
| 2003/0095263 A1 * | 5/2003 | Varshneya et al. | ............ 356/477 |
| 2006/0036183 A1 * | 2/2006 | Sackner et al. | ............... 600/481 |

FOREIGN PATENT DOCUMENTS

| | | |
|---|---|---|
| CN | 1199164 | 11/1998 |
| GB | 2192460 | 1/1988 |
| JP | 2000-000214 | 1/2000 |
| JP | 2000-271103 | 10/2000 |
| TW | 528593 | 4/2003 |

OTHER PUBLICATIONS

"Office Action of Taiwan counterpart application", issued on Mar. 30, 2009, p. 1-p. 4.

* cited by examiner

*Primary Examiner* — Patricia Mallari
*Assistant Examiner* — Michael D'Angelo
(74) *Attorney, Agent, or Firm* — Jianq Chyun IP Office

(57) ABSTRACT

The present invention provides a sleep respiration monitoring system for monitoring sleep quality of a user. The sleep respiration monitoring system has a sensing fabric, a detecting circuit and a judging and analysis circuit. The electrical characteristics of the sensing fabric vary with respiration status or extent of body movement of a user. The detecting circuit detects the electrical characteristics of the sensing fabric. The judging and analysis circuit performs signal processing, signal collection, signal classification and signal determination on output signals of the detecting circuit, so as to determine whether the user lies on the sensing fabric and the sleep quality of the user.

13 Claims, 10 Drawing Sheets

Even pressure

Uneven pressure

RESPIRATION MONITORING SYSTEM

CROSS-REFERENCE TO RELATED APPLICATION

Figure 1:
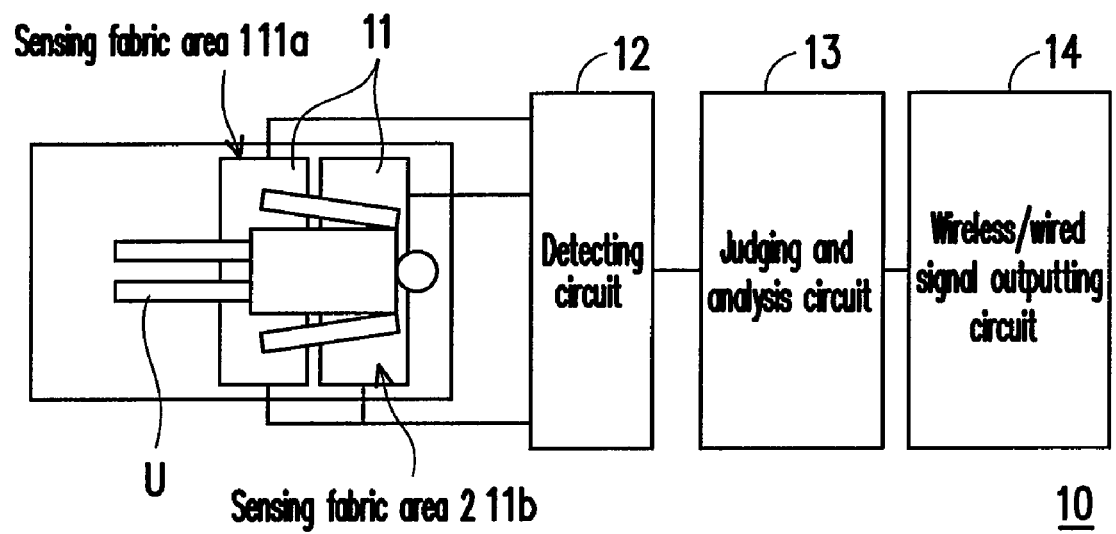

This application claims the priority benefit of Taiwan application Ser. No. 96108406, filed on Mar. 12, 2007. The entirety of the above-mentioned patent application is hereby incorporated by reference herein and made a part of this specification.

BACKGROUND OF INVENTION

1. Field of the Invention

The present invention relates to a sleep respiration monitoring system.

2. Description of Related Art

The present invention determines user's sleep quality in bed, which helps knowing user's sleep efficiency. In addition, detecting user's respiration status in bed also helps to discover SIDS (Sudden Infant Death Syndrome) emergency early, so that family members or rescue workers can be informed earlier to take appropriate medical actions.

In term of present technology, some existing technology uses pressure-sensitive resistor to monitor sleep respiration, movements and SIDS. The shortcoming of using pressure-sensitive resistor is that the forming material is too hard, which results in poor body feel.

In addition, other prior arts use spiral flat inductor strip to monitor respiration. However, such technologies need to form electric field by using inductor and capacitor, so user has to be exposed to electric field, which leads to low consumer acceptance.

Or, other prior arts use complicated semi-conductive pressure sensor to sense use's respiration movement. However, mattress using such technology uses sealed airflow as a monitoring method, mechanism thereof is too complicated.

There further are other prior arts using combination structure of elastic fabric and metal wires to measure the volume change of chest and abdomen. In such technology, extent of self-inductance generated by magnetic field is proportional to cross-sectional area of coil. However, main shortcomings thereof are: 1. Elastic fabric with metal wires woven in loses softness of texture; 2. Circuit measuring magnetic field changes is too complicated, and the size thereof is too large, which result in low product value-added.

Therefore, it's preferable to have a sleep aspiration monitoring system using softer material to increase feel without exposing users to electric field, with simple structure, small size and high product value-added.

SUMMERY OF THE INVENTION

In this regard, the present invention provides a sleep respiration monitoring system which uses softer sensing fabric to improve user's body feel.

The present invention provides a sleep respiration monitoring system for measuring sleep quality and respiration status of a testee. The sleep respiration monitoring system comprises: a sensing fabric, a detecting circuit and judging and analysis circuit. The electric characteristics of the sensing fabric may vary with respiration status or extent of body movement of the testee. The detecting circuit detects the electric characteristic of the sensing fabric. The judging and analysis circuit performs signal processing, signal collection, signal classification and estimation to output signals of the detecting circuit, so as to estimate whether the testee is lying on the sensing fabric and to estimate sleep quality of the testee.

In order to the make the aforementioned and other objects, features and advantages of the present invention comprehensible, a preferred embodiment accompanied with figures is described in detail below.

BRIEF DESCRIPTIONS OF DRAWINGS

FIG. 1 schematically illustrates a diagram of a sleep respiration monitoring system according to an embodiment of the present invention.

Figure 2A:
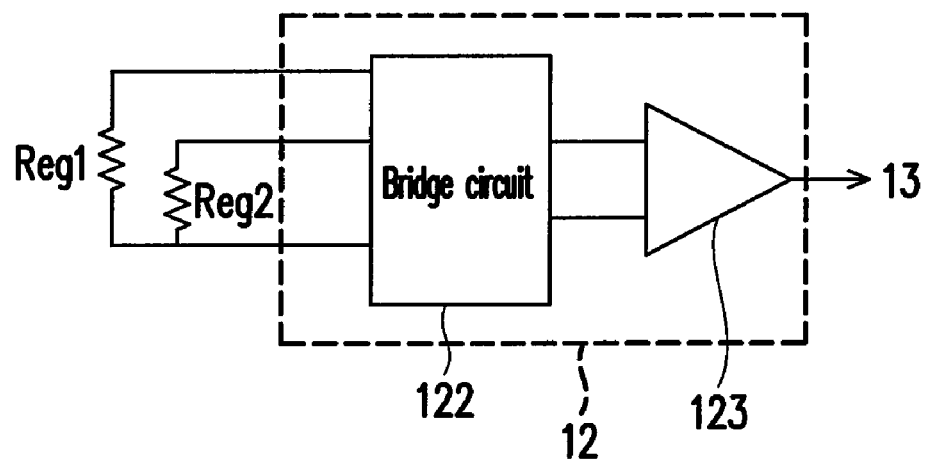

FIG. 2A schematically illustrates a circuit block diagram of a detecting circuit according to the present embodiment.

Figure 2B:
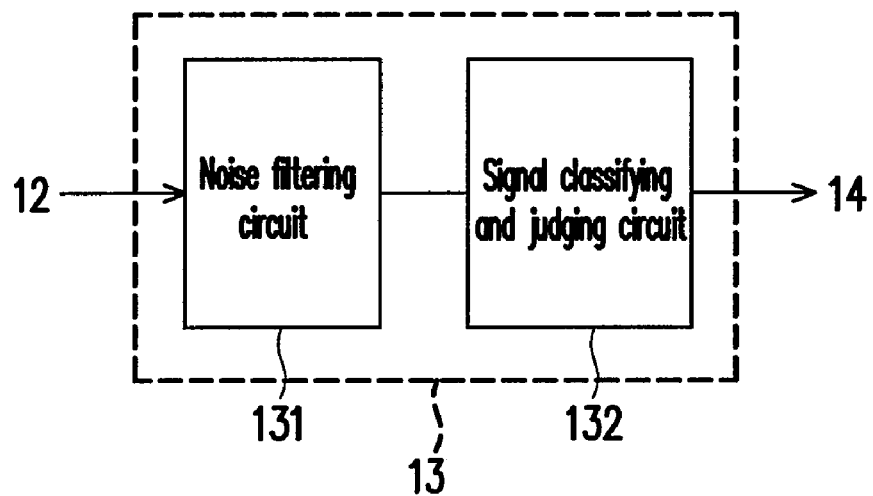

FIG. 2B schematically illustrates a circuit block diagram of a judging and analysis circuit according to the present embodiment.

Figure 3:
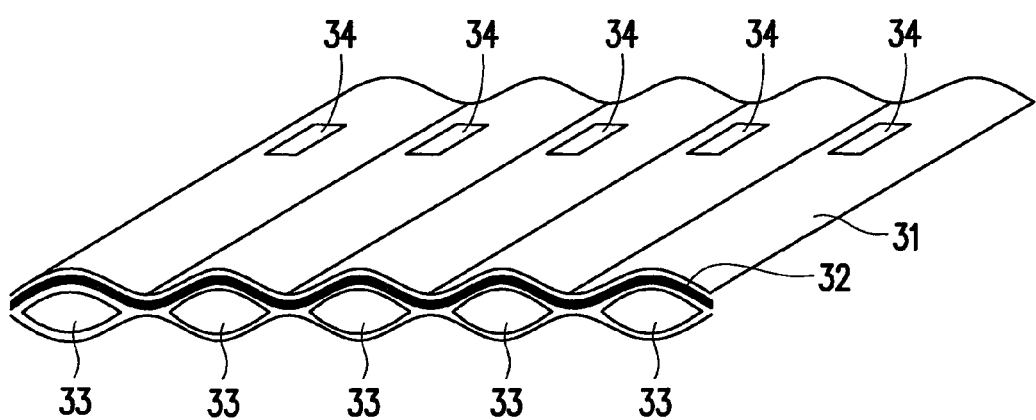

FIG. 3 schematically illustrates a diagram of a sensing fabric according to the present embodiment.

Figure 4A:
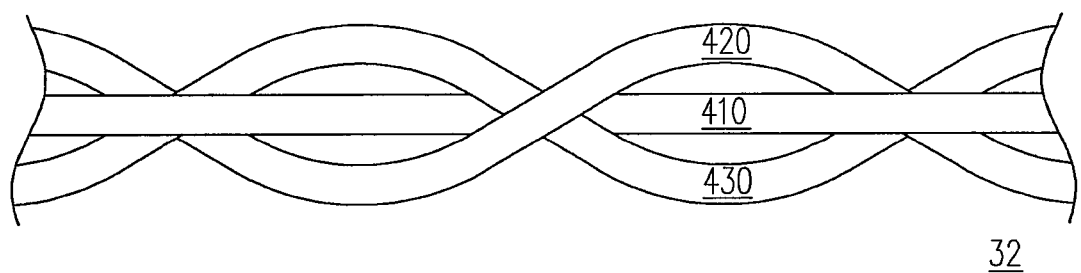
Figure 4B:
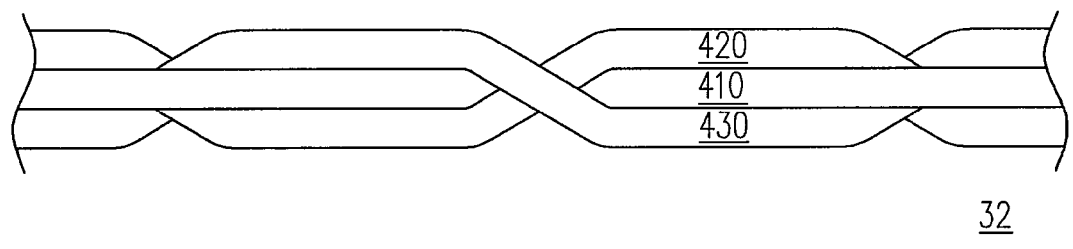

FIG. 4A and FIG. 4B schematically illustrate a diagram of a dual-wrapped conductive yarn.

Figure 5A:
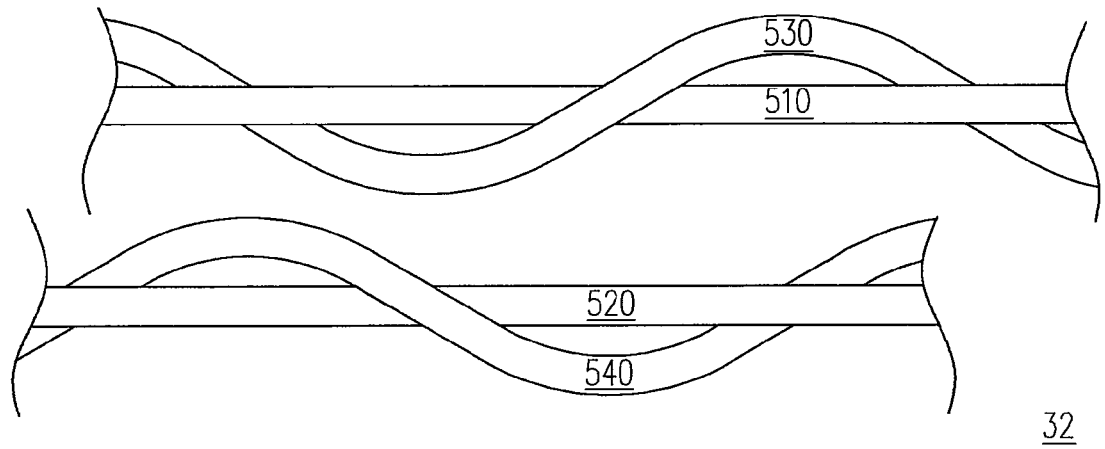
Figure 5B:
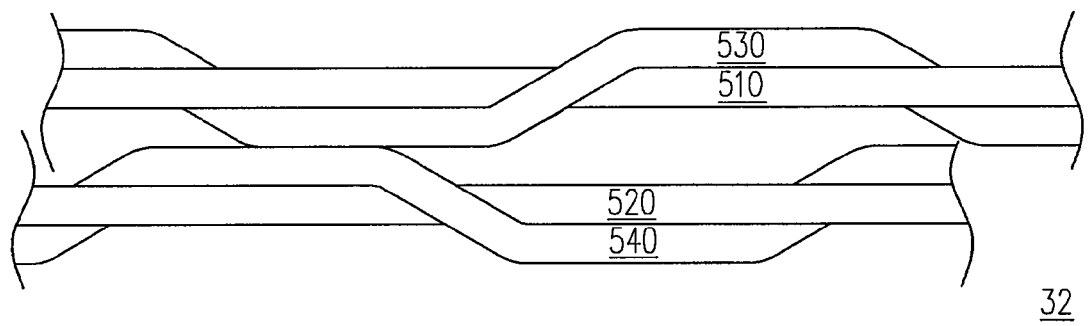

FIG. 5A and FIG. 5B schematically illustrates a diagram of a single-wrapped conductive yarn.

Figure 6:
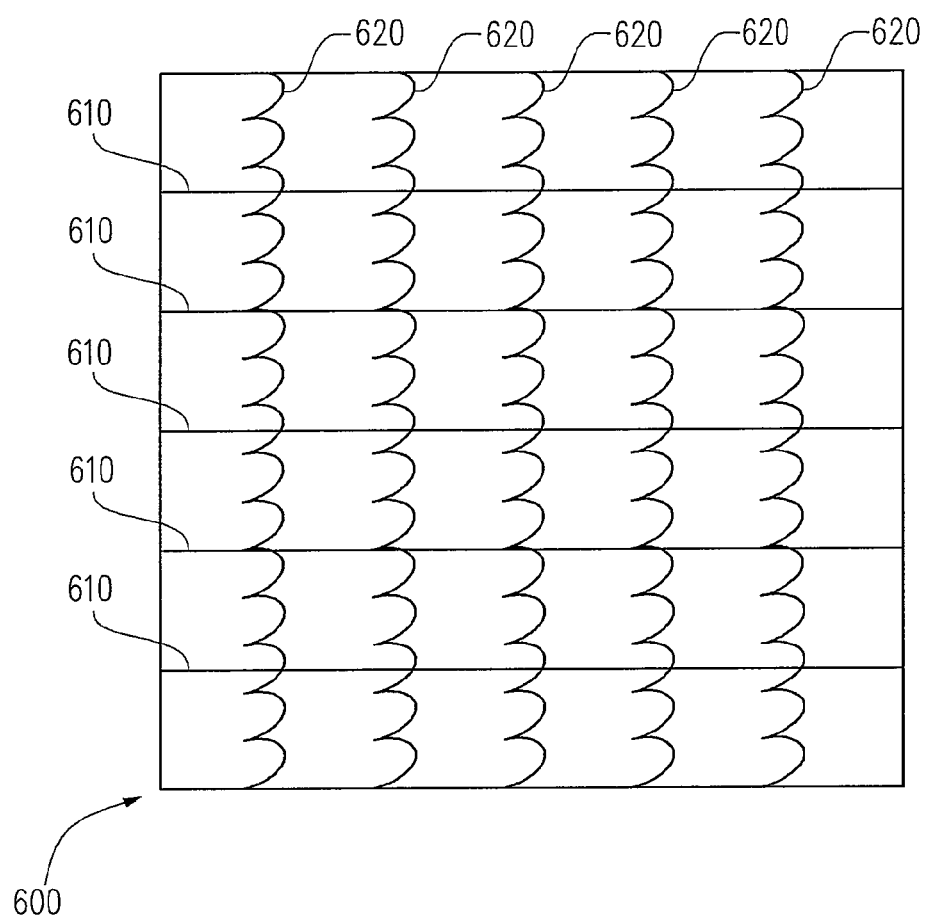

FIG. 6 schematically illustrates a diagram of weaving wrapped conductive yarns with low resistance conductive fibers into the sensing fabric.

Figure 7:
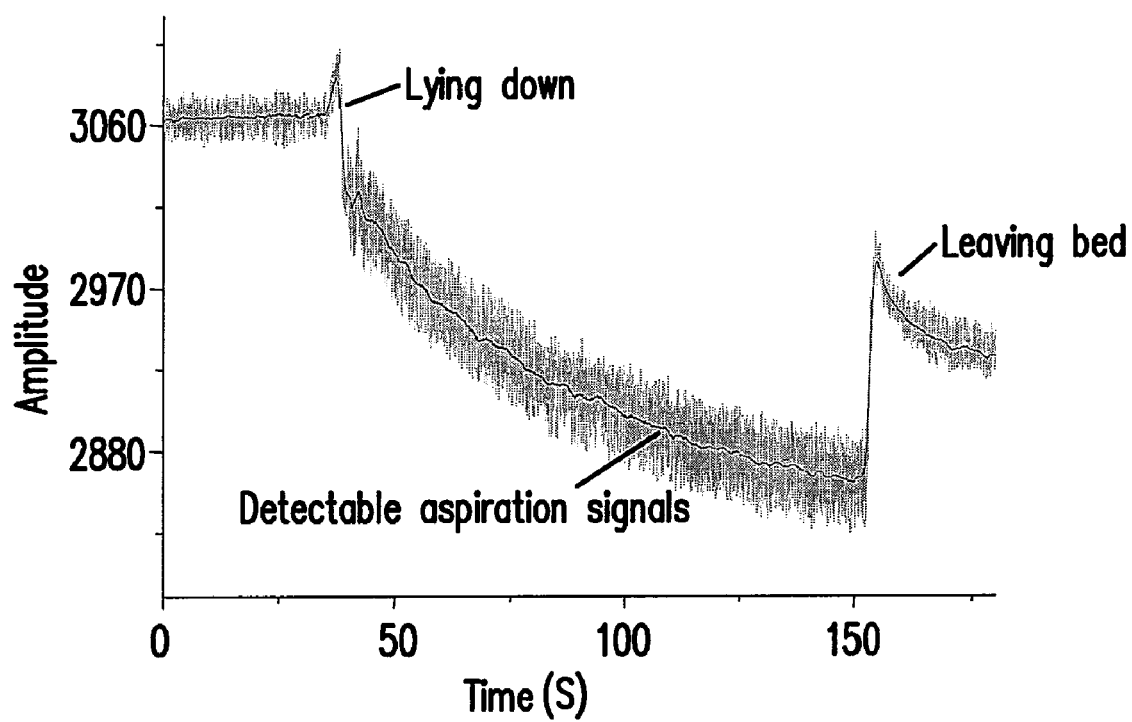

FIG. 7 shows a signal distribution diagram.

Figure 8A:
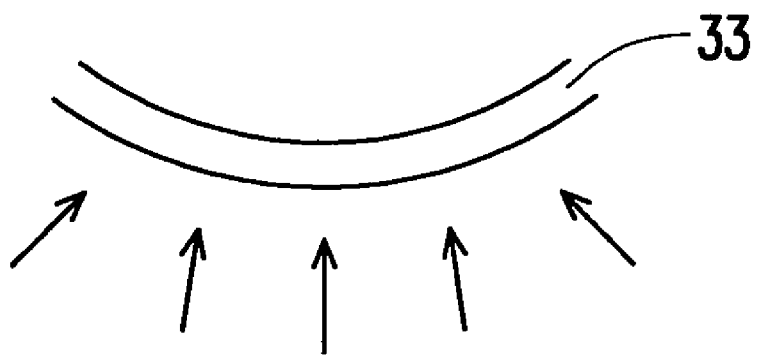
Figure 8B:
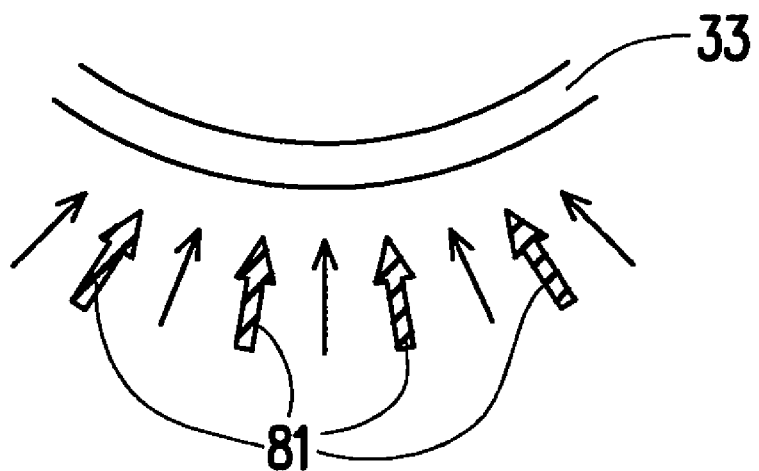

FIGS. 8A and 8B respectively illustrate diagrams of an even-pressed method and an uneven-pressed method of the elastic structure.

Figure 9A:
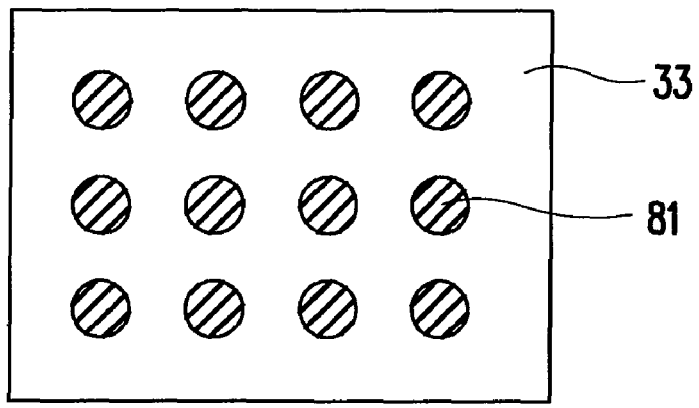
Figure 9A:
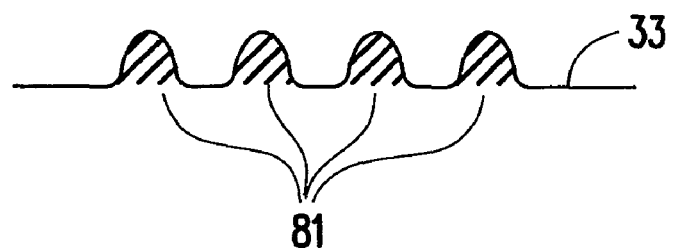
Figure 9B:
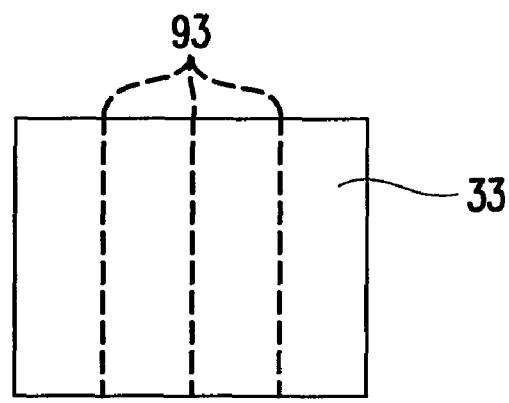
Figure 9B:
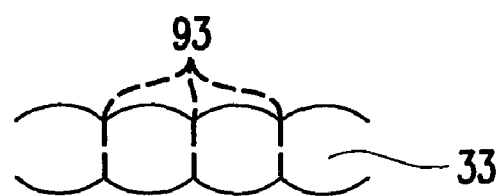

FIGS. 9A and 9B schematically show two design methods of the uneven-pressed elastic structure.

Figure 10A:
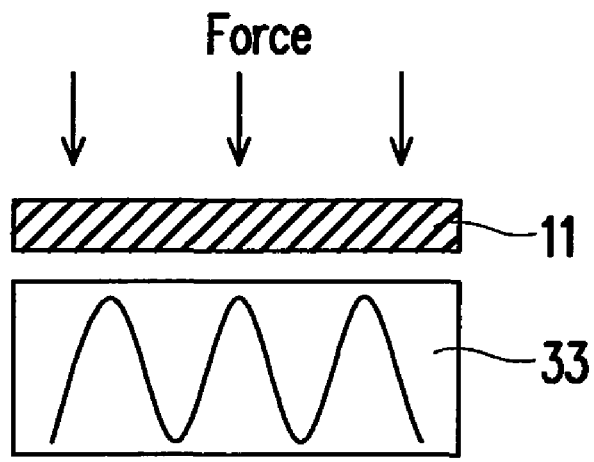
Figure 10B:
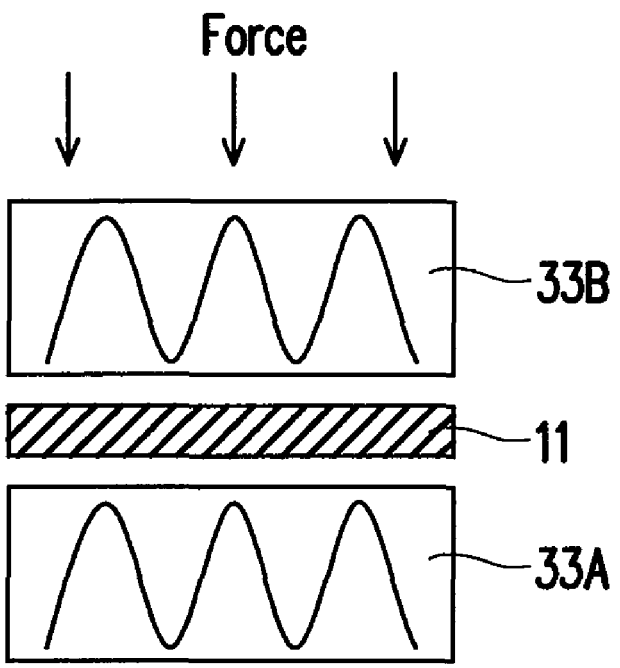

FIGS. 10A and 10B schematically shows diagrams of relative locations between the elastic structure and the sensing fabric.

DESCRIPTION OF EMBODIMENTS

In order to make the contents of the present invention more apparent, the following embodiments are provided as practical examples of embodiment of the present invention.

With reference to FIG. 1, FIG. 1 schematically shows a sleep respiration monitoring system 10 according to an embodiment of the present invention. The sleep respiration monitoring system 10 is suitable for measuring sleep quality of the testee U. The sleep respiration monitoring system 10 comprises: the sensing fabric 11, the detecting circuit 12, the judging and analysis circuit 13 and a wireless/wired signal outputting circuit 14.

The electric characteristics (for example equivalent resistance) of the sensing fabric 11 may change in response to respiration status or extent of body movement of the testee U. In the present embodiment, the sensing fabric 11 is zoned into two areas: the sensing fabric area 1 which is 11a and the sensing fabric area 2 which is 11b. Of cause the numbers of the zoned area on the sensing fabric 11 are not limited to the above example.

The detecting circuit 12 is coupled to the sensing fabric 11. The detecting circuit 12 is suitable for detecting the change of the electric characteristics (for example resistance) of the sensing fabric.

The judging and analysis circuit 13 is coupled to the detecting circuit 12. The judging and analysis circuit 13 performs signal processing, signal collection, signal classification and estimation to the output signals of the detecting circuit 12, so as to estimate whether the testee U is lying on the sensing fabric and to estimate sleep quality of the testee U. The output signal of the judging and analysis circuit 13 may also be displayed on man-machine interface. The output signal of the judging and analysis circuit 13 may further be used to drive external devices (such as sound system, light and etc.). For example, if any abnormality is detected by the judging and analysis circuit 13, the judging and analysis circuit 13 instructs the external devices to make sound or light signals to inform other people or rescue team.

The wireless/wired signal outputting circuit 14 may transmits result acquired by the judging and analysis circuit 13 through wireless/wired transmission, for example transmits to hospital/physician, and etc.

With reference to FIG. 2A, the FIG. 2A schematically illustrates a circuit block diagram of the detecting circuit 12 according to the present embodiment. As shown in FIG. 2A, the detecting circuit 12 comprises: a bridge circuit 122 and an operation amplifier 123.

The bridge circuit 122 may detects the resistance change amount of the equivalent resistance Req1 (which is the equivalent resistance of the sensing fabric area 1 which is 11a) and an equivalent resistance Req2 (which is the equivalent resistance of the sensing fabric area 2 which is 11b).

The operation amplifier 123 is coupled to the bridge circuit 122. The operation amplifier 123 amplifies the output signal of the bridge circuit 122 and transmits the same to the judging and analysis circuit 13.

With reference to FIG. 2B, the FIG. 2B schematically illustrates a circuit block diagram of the judging and analysis circuit 13 according to the present embodiment. As shown in FIG. 2B, the judging and analysis circuit 13 comprises a noise filtering circuit 131 and a signal classifying and judging circuit 132.

The noise filtering circuit 131 eliminates high frequency noise signal of the output signal of the detecting circuit 12. For example noise above 50 Hz may be eliminated.

The signal classifying and judging circuit 132 determines whether the testee turns over, the total sleep time and sleep efficiency according to the output signal of the detecting circuit 12. Moreover, the signal classifying and judging circuit 132 may determine the in-bed time and out-bed time, extent of body movement (extent of over-turn) and respiration rate, and etc. The signal classifying and judging circuit 132 also records daily and weekly sleeping habits of the testee.

With reference to FIG. 3, the FIG. 3 schematically illustrates a diagram of the sensing fabric 11 according to the present embodiment. As shown in FIG. 3, the sensing fabric 11 comprises: a main body 31, wrapped conductive yarns 32, an elastic structure 33 and a temperature sensing element 34.

The main body 31 combines and supports the wrapped conductive yarns 32, the elastic structure 33 and the temperature sensing element 34. The main body 31 for example may be combined in mattress, sheet, seat cushion, back cushion, and etc.

The elastic structure 33 may be through-hole material (such as PU foam) or fabric structure (such as multi-layer buffer fabric) to increase the testee's feel. The elastic structure 33 may be disposed on the substrate layer or top layer of the main body 31. The temperature sensing element 34 may be used to monitor the testee U's body temperature, and is more helpful for determining whether the testee U is lying on the sensing fabric 11.

There are two types of structures of the wrapped conductive yarns 32, one is dual-wrapped, and one is signal-wrapped. FIG. 4A and FIG. 4B schematically illustrate a diagram of the dual-wrapped conductive yarn. FIG. 5A and FIG. 5B schematically illustrate a diagram of the single-wrapped conductive yarn.

FIG. 4A and FIG. 4B respectively illustrate a diagram of the dual-wrapped conductive yarn with and without force applied. With reference to FIGS. 4A and 4B, the dual-wrapped conductive yarn comprises conductive fibers 420, 430, and a non-conductive elastic yarn 410. The conductive fibers 420 and 430 are wrapped on the elastic yarn 410. When no force is applied, the conductive fibers 420 and 430 do not tightly wrapped around the elastic yarn 410, and the conductive fibers 420 and 430 do not contact with each other. The conductive fiber for example is carbon black fiber, copper ion fiber or silver-plated fiber. The resistance rate of the conductive fiber is between $10^2 \sim 10^6$ Ω/cm.

When dual-wrapped conductive yarn is stretched or pressed by the testee, the resistance of the sensing fabric changes accordingly. With reference to FIG. 4B, when force is applied, the conductive fibers 420 and 430 tightly close to the elastic yarn 410. As a result, the conductive fibers 420 and 430 contact to each other and a plurality of contact points are formed between the conductive fibers 420 and 430. The contact points change conductive path of current in the conductive fiber, as a result, the resistance of the dual-wrapped conductive yarn is decreased or increased.

FIG. 5A and FIG. 5B respectively illustrate a diagram of the single-wrapped conductive yarn with and without force applied. With reference to FIG. 5B, the single-wrapped conductive yarn 32 comprises two groups of wrapped conductive yarns. One group of the wrapped conductive yarns is formed through wrapping the conductive fiber 530 around the elastic yarn 510. Another group of the wrapped conductive yarns is formed through wrapping the conductive fiber 540 around the elastic yarn 520. When the wrapped conductive yarns are stretched or pressed by the testee, the resistance of the sensing fabric changes accordingly.

In addition, if area of the sensing fabric 11 is very big, the current signal on the sensing fabric 11 is easily to attenuate. Therefore, low resistance conductive fabric may be woven into the sensing fabric alternately. As shown in FIG. 6, the low resistance conductive fabric 620 intersects the wrapped conductive yarn 610 on the sensing fabric 600. The low resistance conductive fabric 620 for example vertically intersects the wrapped conductive yarn 610; however the present embodiment is not limited to vertical intersection thereof. With FIG. 6 structure, current signals may be detected according to different equivalent impedances and locations. The structure of the wrapped conductive yarn 610 may be as shown in FIG. 4A or FIG. 5B.

With reference to FIG. 7, FIG. 7 schematically illustrates a signal distribution diagram measured by the present embodiment. Working with database, the system of the present embodiment can determine which signals relate to "lie down", "aspiration signal" and "leave the bed" and the body movements alike according to the signal distribution diagram.

The elastic structure 33 in FIG. 3 may be classified into even-pressed force method and uneven-pressed force method according to forms of being subjected to force. FIGS. 8A and 8B respectively illustrate diagrams of the method of even-pressed and the method of uneven-pressed. In FIG. 8B, 81 represents support points.

The uneven-pressed elastic structure has a plurality of design methods. FIGS. 9A and 9B show two different design methods. In FIG. 9A, the elastic structure 33 and the support points 81 may be the same material, or may be different materials. In FIG. 9A, the support points 81 are protrusive, while in another embodiment, the support points 81 may be not protrusive, but the material thereof is harder. In FIG. 9B, the surface of the elastic structure 33 is flat; the sewing line 93 zones the elastic structure 33. The designs of FIGS. 9A and 9B can further promote signal detecting sensitivity.

In addition, relative locations of the elastic structure 33 and the sensing fabric are shown in FIGS. 10A and 10B. As shown in FIG. 10A, the elastic structure 33 may be disposed under the sensing fabric 11. As shown in FIG. 10A, the elastic structures 33A and 33B may be respectively disposed above and under the sensing fabric 11. The elastic structures 33A and 33B may be the same material, may also be different materials. In addition, the elastic structure 33B is harder than the elastic structure 33A.

In addition, when the present system is used to detect human respiration, the sensing fabric may surround the chest or abdomen of the user, the portion of body which moves up and down with one's respiration.

The sensing fabric of the present embodiment has the following advantages: breathable, soft, elastic, stretchable, washable, bendable, and etc.

To summarize the above descriptions, the present sleep aspiration monitoring system monitors aspiration of user while user almost doesn't feel bound. In addition, the present sleep aspiration monitoring system monitors through sensing fabric's deformation, which is more advanced than prior arts.

The present sleep aspiration monitoring system may be combined into home use sheets, mattresses and seat cushions and other textiles. In addition, the sensing fabric may be disposed on or in mattresses, sheets, and seat cushions, so that sleep aspiration monitoring can be performed at home instantaneously.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed:

1. A sleep respiration monitoring system for measuring sleep quality of a testee, the sleep respiration monitoring system comprising:
    a sensing fabric comprising at least one sensing fabric area, an electric characteristic of the sensing fabric being changed in response to a respiration status or an extent of body movement of the testee;
    a detecting circuit, coupled to the at least one sensing fabric area of the sensing fabric, the detecting circuit comprising a bridge circuit, and the bridge circuit being used for detecting the change of equivalent resistance of the at least one sensing fabric area of the sensing fabric so as to output an output signal accordingly; and
    a judging and analysis circuit, coupled to the detecting circuit, performing signal processing, signal collection, signal classification and judging to the output signal, so as to determine whether the testee is lying on the sensing fabric and to judge sleep quality of the testee accordingly,
    wherein the change of the equivalent resistance of the at least one sensing fabric area of the sensing fabric is caused by whether the testee is lying on the at least one sensing fabric area of the sensing fabric,
    wherein the at least one sensing fabric area comprises:
        at least two wrapped conductive yarns respectively formed by wrapping at least a conductive fiber around an elastic yarn, wherein when at least one of the wrapped conductive yarns is stretched or pressed by the testee, the resistance of the sensing fabric changes accordingly; and
        at least two low resistance conductive fabrics intersecting and directly and electrically connecting the at least two wrapped conductive yarns for making the bridge circuit accurately detect the change of the equivalent resistance of the sensing fabric according to currents flowing through different locations on the sensing fabric.

2. The sleep respiration monitoring system of claim 1, wherein the detecting circuit further comprises:
    an operation amplifier, coupled to the bridge circuit, for amplifying and outputting the output signal.

3. The sleep respiration monitoring system of claim 1, wherein the at least two low resistance conductive fabrics vertically intersect the at least two wrapped conductive yarns.

4. The sleep respiration monitoring system of claim 1, wherein the judging and analysis circuit comprises:
    a noise filtering circuit, for eliminating high frequency noise signal of the output signal of the detecting circuit.

5. The sleep respiration monitoring system of claim 1, wherein the judging and analysis circuit comprises:
    a signal classifying and judging circuit, determining whether the testee is turning over, the testee's total sleep time and sleep efficiency according to the output signal of the detecting circuit.

6. The sleep respiration monitoring system of claim 1, wherein the at least one sensing fabric area of the sensing fabric further comprises an elastic structure.

7. The sleep respiration monitoring system of claim 1, wherein the at least one sensing fabric area of the sensing fabric further comprises a temperature sensing element.

8. The sleep respiration monitoring system of claim 1, wherein the at least one sensing fabric area of the sensing fabric may be disposed on or in mattress, sheet, seat cushion.

9. The sleep respiration monitoring system of claim 6, wherein the elastic structure comprises a through-hole material.

10. The sleep respiration monitoring system of claim 6, wherein the elastic structure comprises a plurality of layers of buffer fabrics.

11. The sleep respiration monitoring system of claim 6, wherein the elastic structure further comprises a plurality of local support points, the local support points protrude or do not protrude out of surface of the elastic structure; and the material of the local support points is the same as or different from the material of the elastic structure.

12. The sleep respiration monitoring system of claim 6, wherein the elastic structure further comprises a plurality of sewing lines zoning the elastic structure.

13. The sleep respiration monitoring system of claim 6, wherein the elastic structure is disposed on one side or two opposite sides of the sensing fabric.

* * * * *